United States Patent [19]
Schack et al.

[11] 3,961,620
[45] June 8, 1976

[54] CERVICAL SAMPLING APPARATUS

[75] Inventors: Colin B. Schack; Clarence E. Purdy, both of Omaha, Nebr.

[73] Assignee: Research Industries Corporation, Salt Lake City, Utah

[22] Filed: Mar. 30, 1973

[21] Appl. No.: 346,698

Related U.S. Application Data

[63] Continuation of Ser. No. 123,697, March 12, 1971, abandoned.

[52] U.S. Cl. ............................ 128/2 B; 128/304
[51] Int. Cl.² ................................. A61B 10/00
[58] Field of Search .......... 128/2 B, 2 W, 2 R, 2 M, 128/304, 218 N

[56] References Cited
UNITED STATES PATENTS

| | | | |
|---|---|---|---|
| 2,955,591 | 10/1960 | MacLean | 128/2 B |
| 3,037,496 | 6/1962 | Melges | 128/2 W |
| 3,320,954 | 5/1967 | Cowley | 128/218 N |
| 3,394,699 | 7/1968 | Koett | 128/2 B |
| 3,438,366 | 4/1969 | Kariher et al. | 128/2 B |
| 3,513,830 | 5/1970 | Kalayjian | 128/2 W |
| 3,540,432 | 11/1970 | Ayre | 128/2 B |
| 3,554,185 | 1/1971 | Kohl | 128/2 B |
| 3,592,186 | 7/1971 | Oster | 128/2 B |

*Primary Examiner*—Kyle L. Howell
*Attorney, Agent, or Firm*—Richards, Harris & Medlock

[57] ABSTRACT

A cervical sampling apparatus includes a curved, hollow tube having an outside diameter of ⅝ inches, a working length of 3½ inches, and a radius of curvature of 9½ inches. A paddle-shaped sampling member is normally housed within one end of the tube, and a flexible shaft extends from the sampling member through the opposite end of the tube for selectively extending the sampling member to a sampling position outside the tube, for rotating the sampling member in the sampling position and for retracting the sampling member into the tube. Preferably, the sampling member is transparent and is separable from the shaft, so that a specimen taken on the sampling can be analyzed without removal therefrom.

4 Claims, 5 Drawing Figures

INVENTORS:
COLIN B. SCHACK
CLARENCE E. PURDY

Richards, Harris & Hubbard
ATTORNEYS

CERVICAL SAMPLING APPARATUS

This is a continuation of application Ser. No. 123,697, filed Mar. 12, 1971, now abandoned.

BACKGROUND AND SUMMARY OF THE INVENTION

This invention relates to a cervical sampling apparatus.

It has long been recognized that women should be examined periodically for evidence of cervical cancer. Unfortunately, many women neglect to have such examinations performed because of the inconvenience involved in traveling to a doctor's office, etc. It is known to provide a device which permits the taking of cervical cancer test specimens in the home for subsequent mailing to a doctor. The present invention comprises an improvement over such a device which is characterized by critical dimensions that permit its use by virtually any adult woman.

In accordance with the preferred embodiment of the invention, a cervical sampling apparatus comprises an elongate, curved, substantially rigid, hollow tube including structure for locating one end thereof within the vaginal canal adjacent the cervix, a paddle-shaped sampling member nomally housed within said one end of the tube, and apparatus for extending the sampling member out of the tube to a sampling position and for subsequently retracting the sampling member into the tube. The apparatus is preferably formed entirely of inexpensive, sterilizable, disposable materials, and the tube is characterized by an outside diameter of about ⅝ inch, a radius of curvature of about 9½ inches, and a working length of about 3½ inches. In the preferred embodiment of the invention, the apparatus for extending and retracting the sampling member comprises a flexible shaft which extends through the tube for manipulation from the opposite end thereof.

In the preferred use of the invention, the tube is inserted into the vaginal canal with the sampling member positioned in the tube. When the tube is properly positioned, the flexible shaft is manipulated to extend the sampling member to the sampling position and to rotate the sampling member in the sampling position, whereby a specimen is gathered on the sampling member. The shaft is then manipulated to retract the sampling member into the tube, after which the tube is withdrawn from the vaginal canal. Subsequently, a fixative is applied to the specimen on the sampling member, and the sampling member is then separated from the shaft and is forwarded to a laboratory. At the laboratory, the specimen is analyzed intact on the sampling member.

DESCRIPTION OF THE DRAWING

A more complete understanding of the invention may be had by referring to the following detailed description when taken in conjunction with the accompanying drawing, wherein.

DETAILED DESCRIPTION

Figure 1:
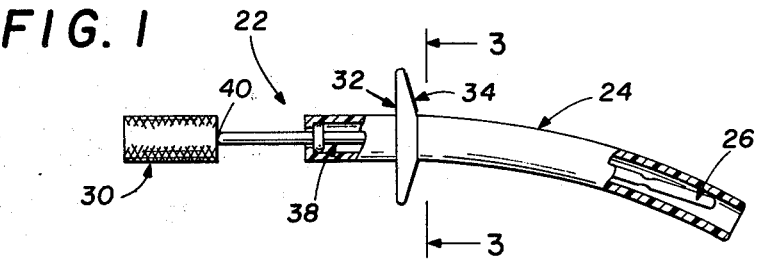
FIG. 1 is a reduced side view of a cervical sampling apparatus comprising the preferred embodiment of the invention.

Referring now to the drawing, and more particularly to FIG. 1 thereof, there is shown a cervical sampling apparatus 22 comprising the preferred embodiment of the invention. The cervical sampling apparatus comprises an elongate, curved, substantially rigid, hollow tube 24, a paddle-shaped sampling member 26 which is normally positioned within one end of the tube 24, and a flexible shaft 28 which extends from the sampling member 26 through the opposite end of the tube 24 to a handle 30. A locating shield 32 is formed integrally with the tube 24 to define the working length of the cervical sampling apparatus 22, and a marker 34 is fixed to the shield 32 to define the top of the apparatus 22.

Figure 2:
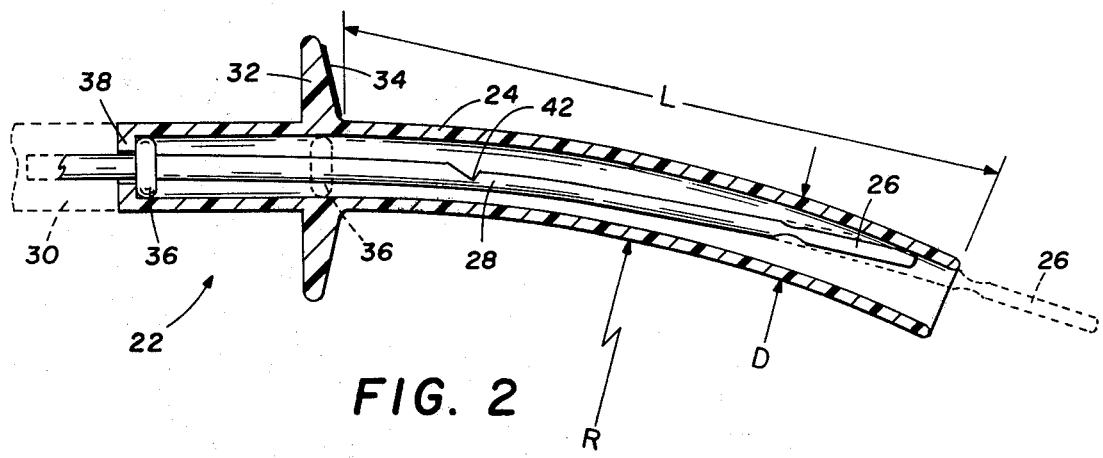
FIG. 2 is a full scale longitudinal sectional view of the apparatus shown in FIG. 1.

As is best shown in FIG. 2, the flexible shaft 28 is preferably formed integrally with the paddle-shaped sampling member 26, and is provided with an annular ring 36. A cooperating shoulder 38 is formed on the tube 24 to limit the movement of the shaft 28 and the paddle-shaped sampling member 26 into the tube 24. Two weakened sections 40 and 42 are formed in the flexible shaft 28 adjacent the handle 30 and between the annular ring 36 and the paddleshaped sampling member 26, respectively. The tube 24 of the apparatus 22 is preferably formed from an inexpensive, sterilizable, disposable material, such as styrene, whereas the shaft 28 and the sampling member 26 are preferably formed from clear acrylic plastic.

In use, the cervical sampling apparatus 22 is initially sterilized and is forwarded in a sterile container. To prevent contamination of the sampling member 26, a tube 24 is inserted into the vaginal canal with the sampling member 26 positioned as shown in FIG. 1 and in full lines in FIG. 2. The tube 24 is inserted to the depth permitted by the shield 32 and with the marker 34 oriented upwardly. This positions the end of the tube 24 which houses the paddle-shaped sampling member 26 in the portion of the vaginal canal next adjacent the cervix.

Figure 4:
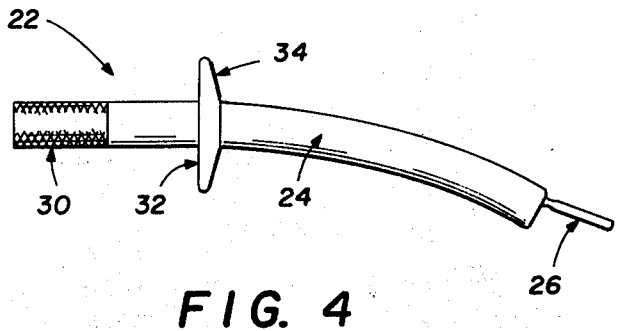
FIG. 4 is a view similar to FIG. 1 and illustrating the operation of the apparatus.
Figure 3:
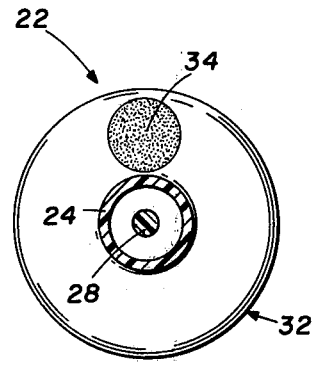
FIG. 3 is a full scale sectional view taken generally along the line 3-3 of FIG. 1.
Figure 5:
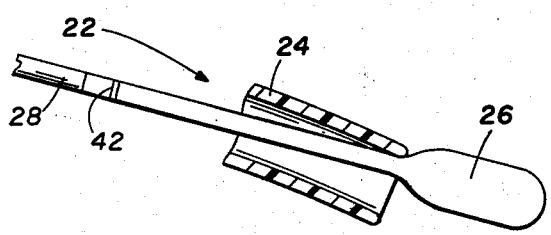
FIG. 5 is a partial sectional view similar to FIG. 2 and further illustrating the operation of the apparatus.

After the tube 24 is properly inserted, the handle 30 is manipulated, first to extend the paddle-shaped sampling member 26 to the sampling position shown in FIG. 4 and in dashed lines in FIG. 2, and thereafter to rotate the sampling member 26 relative to the tube 24. By this means, a test specimen is gathered on the surfaces of the sampling member 26. Next, the handle 30 is manipulated to retract the member 26 into the tube 24, after which the tube 24 is withdrawn from the vaginal canal.

When the tube 24 has been withdrawn, the handle 30 is manipulated to return the member 26 to the position shown in FIG. 4. Then, a fixative is applied to the specimen on the member 26 and is allowed to dry. Finally, the handle 30 is separated from the shaft 28 at the weakened section 40, the shaft is removed from the tube, and the paddle-shaped sampling member 26 is removed from the shaft 28 at the weakened section 42. The member 26 is then forwarded to a cytology laboratory, whereupon the sample on the member 26 is processed and analyzed without removal from the member 26. This feature of the present invention is considered to be very important in that it is very economical and in that it eliminates any possibility of contamination of the specimen during transfer to a glass slide.

Through clinical experimentation, it has been determined that the dimensions of the tube 24 of the cervical sampling apparatus 22 are critical to the proper functioning of the device. To this end, the tube 24 preferably has a working length L of 3½ inches, an outside diameter D of ⅝ inch, and a radius of curvature R of 9½ inches. It has been found that a tube 24 having such dimensions will position the sampling member 26 at the proper location in the vaginal canal of virtually any adult woman.

From the foregoing, it will be understood that the present invention comprises a cervical sampling apparatus including a curved tube having critical working length, outside diameter, and radius of curvature dimensions, a sampling member normally housed within one end of the tube, and structure at the opposite end of the tube for selectively extending the sampling member to a sampling position located without the tube and for subsequently retracting the sampling member into the tube. In accordance with the preferred embodiment of the invention, the sampling member is a paddle-shaped, rigid member and the extending and retracting structure comprises a flexible shaft fixed to the paddle-shaped member and extending therefrom through the tube and out the opposite end thereof. The preferred use of the invention is characterized by removing the sampling member from the shaft after a sample has been taken, so that the specimen can be analyzed on the sampling member.

Although the preferred embodiment of the invention has been illustrated in the accompanying drawing and described in the foregoing specification, it will be understood that the invention is not limited to the embodiment disclosed, but is capable of rearrangement, modification and substitution of parts and elements without departing from the spirit of the invention.

What is claimed is:

1. A cervical sampling apparatus comprising:
   an elongate, substantially rigid hollow tube having a first, relatively long end which is curved about an axis extending perpendicularly to the tube and having a second relatively short end which is substantially straight;
   an annular shield fixed to the outside of the tube at the intersection of the first and second ends for locating the first end in the vaginal canal adjacent the cervix;
   a substantially rigid, paddle-shaped sampling member normally enclosed by the first end of the tube, said sampling member comprising opposed, flat, parallel major surfaces, opposed parallel side edges, and a semicircular end edge extending between the side edges whereby the sampling member is adapted to collect a cervical test specimen and thereafter for cytological analysis of the collected cervical test specimen with the cervical test specimen intact on the sampling member;
   an elongate flexible shaft fixed to the sampling member and extending therefrom through the tube and out the second end thereof for selectively reciprocating the sampling member out of the first end of the tube to a sampling position in the vaginal canal adjacent the cervix, for rotating the sampling member in the sampling position and thereby collecting a cervical test specimen on the sampling member, and for thereafter reciprocating the sampling member into the first end of the tube so that the cervical test specimen on the sampling member can be removed from the vaginal canal without contamination;
   a handle means secured to the end of the flexible shaft remote from the sampling member for engagement with the second end of the tube;
   an enlarged portion formed on the flexible shaft at a point spaced from the handle means; and
   a reduced diameter portion at the second end of the tube providing means for cooperation with the enlarged portion of the flexible shaft to limit retraction of the sampling member into the tube;
   said sampling member, said flexible shaft and said enlarged portion on the flexible shaft having an overall length less than the distance from the reduced diameter portion to said first end of the tube so that the sampling member is fully enclosed by the tube when the enlarged portion on the flexible shaft is in engagement with the reduced diameter portion of the tube;
   said enlarged portion being positioned on the flexible shaft at a point spaced apart from the handle means by a distance at least as great as the overall length of the sampling member so that the sampling member is fully extended to the sampling portion whenever the handle means is in engagement with the reduced diameter portion of the tube.

2. The cervical sampling apparatus according to claim 1 wherein the elongate flexible shaft further includes a weakened section providing means whereby the sampling member is adapted for detachment from the flexible shaft and from the elongate tube prior to cytological analysis of the cervical test specimen on the sampling member and wherein the handle means is removable from the shaft to facilitate removal of the sampling member from the tube.

3. The cervical sampling apparatus according to claim 1 further including reference indicia on the annular shield for use in properly orienting the elongate tube relative to the vaginal canal.

4. A self-administered cervical test specimen gathering device comprising:
   a. an elongated, substantially rigid, hollow tube with a curved length of about three and one-half inches from a shield encircling said tube to an open end of said tube, said curved length having a radius of curvature of about nine and one-half inches and adapted to slide easily into a woman's vaginal canal locating said open end thereof adjacent to the cervix;
   b. a substantially rigid, extensible, rotatable paddle-shaped, test specimen gathering means housed within said open end of said tube;
   c. a shaft, rotatably housed within said tube having a length greater than said tube and fixed to said test specimen gathering means, said shaft extending therefrom through said tube and beyond thereof opposite the end housing said test specimen gathering means, said shaft having handle means at its end opposite the specimen gathering means for selectively extending the test specimen gathering means beyond the open tube end housing the test specimen gathering means to a specimen gathering position, for rotating said specimen gathering means while in a specimen gathering position and for selectively retracting the test specimen gathering means from the specimen gathering position into said open end of the tube.

* * * * *